US011986886B2

(12) United States Patent
Lee et al.

(10) Patent No.: US 11,986,886 B2
(45) Date of Patent: May 21, 2024

(54) RAPID SYNTHESIS OF METAL NANOPARTICLES

(71) Applicant: Albert Einstein College of Medicine, Bronx, NY (US)

(72) Inventors: Kyuwan Lee, Rexford, NY (US); Robert H. Singer, New York, NY (US)

(73) Assignee: ALBERT EINSTEIN COLLEGE OF MEDICINE, Bronx, NY (US)

(*) Notice: Subject to any disclaimer, the term of this patent is extended or adjusted under 35 U.S.C. 154(b) by 85 days.

(21) Appl. No.: 17/614,843

(22) PCT Filed: Jun. 5, 2020

(86) PCT No.: PCT/US2020/036276
§ 371 (c)(1),
(2) Date: Nov. 29, 2021

(87) PCT Pub. No.: WO2020/247723
PCT Pub. Date: Dec. 10, 2020

(65) Prior Publication Data
US 2022/0226891 A1    Jul. 21, 2022

Related U.S. Application Data

(60) Provisional application No. 62/858,047, filed on Jun. 6, 2019.

(51) Int. Cl.
*B22F 9/24* (2006.01)
*A61K 9/51* (2006.01)
(Continued)

(52) U.S. Cl.
CPC .............. *B22F 9/24* (2013.01); *A61K 9/5115* (2013.01); *A61K 9/5192* (2013.01); *B22F 1/054* (2022.01);
(Continued)

(58) Field of Classification Search
None
See application file for complete search history.

(56) References Cited

U.S. PATENT DOCUMENTS 6,287,798 B1    9/2001    James et al.
8,257,670 B1    9/2012    Dakshinamurthy et al.
(Continued)

FOREIGN PATENT DOCUMENTS

CN    109128216 A  *  1/2019
EP    3354375 A1     8/2018
(Continued)

OTHER PUBLICATIONS

English Translation of CN 109128126 (originally published Jan. 4, 2019), obtained from PE2E search.*
(Continued)

*Primary Examiner* — George Wyszomierski
(74) *Attorney, Agent, or Firm* — CANTOR COLBURN LLP

(57) ABSTRACT

Described herein is a method of making a reduced metal nanoparticle, the method including mixing a reactive reducing agent with a metal salt in a solution at a temperature of 4-100° C., and forming the reduced metal nanoparticles in the solution. Also described is a kit including a reactive reducing agent that is sensitive to ßgalactosidase, a metal salt, and optionally a modifying agent/functionalizing agent for reduced metal nanoparticles. A 3,4-cyclohexeneoesculetin-B-D-galacto pyranoside (SGNP) gold nanoparticle and its use for measuring ßgalactosidase enzyme activity, comprising by detecting a structural change in the SGNPs caused by the ßgalactosidase are described. Further described are a point of care device, a chip, a biosensor, a laboratory animal, a gene delivery agent, a drug delivery agent, a diagnostic agent, or a disease targeting agent including SGNPs.

10 Claims, 4 Drawing Sheets

(51) Int. Cl.
  *B22F 1/054* (2022.01)
  *B22F 1/0545* (2022.01)
  *B22F 1/102* (2022.01)
  *B82Y 5/00* (2011.01)
  *B82Y 15/00* (2011.01)
  *B82Y 40/00* (2011.01)

(52) U.S. Cl.
  CPC ............ *B22F 1/0545* (2022.01); *B22F 1/056* (2022.01); *B22F 1/102* (2022.01); *B22F 2009/245* (2013.01); *B82Y 5/00* (2013.01); *B82Y 15/00* (2013.01); *B82Y 40/00* (2013.01)

(56) References Cited

U.S. PATENT DOCUMENTS

| | | | |
|---|---|---|---|
| 2007/0051202 A1 | 3/2007 | Raghumaran et al. | |
| 2008/0279946 A1 | 11/2008 | Hainfield | |
| 2016/0121402 A1* | 5/2016 | Kim | B22F 9/24 |
| | | | 75/370 |
| 2017/0081526 A1 | 3/2017 | Ng | |
| 2018/0185926 A1* | 7/2018 | Wang | B22F 1/054 |
| 2018/0311174 A1* | 11/2018 | Irvine | A61K 38/00 |
| 2019/0022234 A1* | 1/2019 | Morel | A61K 47/22 |
| 2021/0402466 A1* | 12/2021 | Grigorenko | B22F 1/00 |

FOREIGN PATENT DOCUMENTS

| | | |
|---|---|---|
| WO | WO-2005/095031 A1 * | 10/2005 |
| WO | 2015196017 A1 | 12/2015 |
| WO | 2018067570 A1 | 4/2018 |
| WO | 2018102765 A1 | 6/2018 |

OTHER PUBLICATIONS

Frens et al.; "Controlled Nucleation for the Regulation of the Particle Size in Monodisperse Gold Suspensions"; Nature; 3 pages (1972).

International Search Report and Written Opinion for International Application PCT/US2020/036276; International Filing Date: Jun. 5, 2020; dated Sep. 21, 2020; 18 pages.

James et al.; "Note: Cyclohexenoesculentin-B-D-Glucoside: A New Substrate for the Detection of Bacterial B-D-Glucosidase"; Journal of Applied Microbiology; 82; pp. 532-536; (1997).

Razgulin, A. et al.; "Strategies for in vivo imaging of enzyme activity: an overview and recent advances"; Chemical Society Reviews, vol. 40, Issue No. 7; 2011; pp. 4186-4216.

* cited by examiner

RAPID SYNTHESIS OF METAL NANOPARTICLES

CROSS REFERENCE TO RELATED APPLICATIONS

This application is a National Stage application of PCT/US2020/036276, filed Jun. 5, 2020, which claims the benefit of priority to U.S. Provisional Application No. 62/858,047, filed Jun. 6, 2019, both of which are incorporated by reference in their entirety herein.

FIELD OF THE DISCLOSURE

The present disclosure is related to methods for rapid, one-step synthesis of reduced metal nanoparticles, particularly biocompatible reduced metal nanoparticles.

BACKGROUND

Gold nanoparticles (GNPs) have attracted considerable interest due to their wide range of application, for example in sensing, molecular labeling, and bio-engineering. Sensing technologies can employ attached surface biomolecules as recognition materials. Ligands such as DNA, proteins, polymers, peptides, and antibodies can act as capping agents to stabilize the GNPs in aqueous solution and provide surface functionality, biological capture and chemical reactivities.

The most common GNP synthesis techniques utilize citrate under acidic reaction conditions. Common methodologies for GNP synthesis are non-polar synthesis using the Brust method, aqueous generation with the Turkevich method, and biological synthesis using a microbial agent. The chemistry of formation for citrate reduction techniques is to reduce the $Au^{3+}$ ion to $A^0$ and stabilize the surface of the colloidal gold with a capping molecule that is soluble in the synthesis media. Traditional aqueous synthesis involves low pH and/or high temperatures; which limit the number of biological capping agents, requiring a ligand exchange step after synthesis for most sensing applications. There have been attempts to generate room-temperature synthesis without any use of toxic catalyst, but the current state-of-art still needs to overcome multiple challenges.

Previously, thiolated DNA-modified nanoparticles were used to detect and form a designed structure both in-vitro and in-vivo. However, the drawback of building nanoparticle structures for sensing is the complexity in methods and materials, as well as the long time required for preparation.

What is needed is a user-friendly and fast synthesis of biocompatible and enzyme-sensitive gold nanoparticles so that a fresh aliquot of nanoparticles can be prepared instantaneously for the best performance without degradation for use in various applications ranging from point-of-care to animal experiments.

BRIEF SUMMARY

In an aspect, a method of making a reduced metal nanoparticle comprises mixing a reactive reducing agent with a metal salt in a solution at a temperature of 4-100° C., and forming the reduced metal nanoparticles in the solution.

In another aspect, a kit includes a reactive reducing agent that is sensitive to βgalactosidase, a metal salt, and optionally a modifying agent/functionalizing agent for reduced metal nanoparticles.

In another aspect, a 3,4-cyclohexeneoesculetin-B-D-galactopyranoside (SGNP) gold nanoparticle is described.

In yet another aspect, a method of measuring βgalactosidase enzyme activity, comprises contacting the SGNPs with a sample suspected of containing βgalactosidase, and detecting a structural change in the SGNPs caused by the βgalactosidase.

In a further aspect, point of care device, a chip, a biosensor, a laboratory animal, a gene delivery agent, a drug delivery agent, a diagnostic agent, or a disease targeting agent comprising the SGNPs.

The above-described and other features will be appreciated and understood by those skilled in the art from the following detailed description, drawings, and appended claims.

DETAILED DESCRIPTION

Described herein is a user-friendly and instantaneous synthesis method for reduced metal nanoparticles, such as biocompatible and enzyme sensitive reduced gold nanoparticles, e.g., Sgal-reduced gold nanoparticles (SGNPs), at room temperature. Prior art room temperature gold nanoparticle synthesis methods are generally either toxic or provide unstable nanoparticles. Sgal sodium salt, for example, is a green chemical which can replace the following room-temperature reducing agents: $NaBH_4$, which is a strong but toxic reducing agent; ascorbic acid, which forms nanoparticle instantaneously, but the resulting nanoparticles are not stable; and oxocarbon which also produces unstable nanoparticles.

There is a demand for a user-friendly and fast synthesis of biocompatible and enzyme-sensitive gold nanoparticles because it is often critical to prepare a fresh aliquot of nanoparticles instantaneously for the best performance without degradation in various applications ranging from point-of-care to animal experiments. Particle preparation for point-of-care diagnostics and animal experiments can be improved by efficiency for micro-volume synthesis, a fast reaction in room temperature, and biocompatibility and biosensitivity in addition to conventional nanoparticle properties such as colloidal stability, and functionality. More importantly, fresh synthesis of functional nanoparticles with the various available functional modifications will extend the range of applications enabling utilization of short lifetime molecules for the instantaneous modifications. For the instantaneous synthesis of functional nanoparticles, it is helpful to select a highly reactive, biocompatible, and biologically functional reducing agent.

Figure 1I:
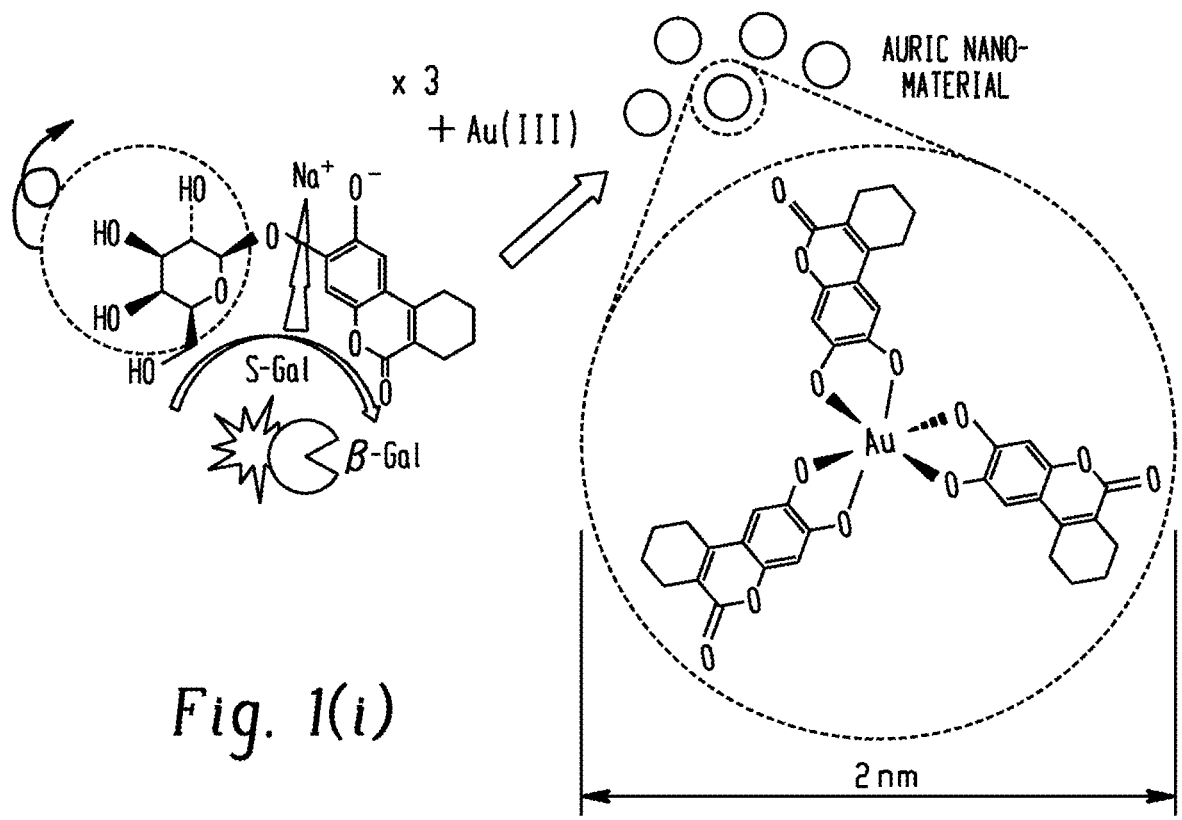
FIG. 1 shows the mechanism of auric nanomaterial (ANM) and Sgal-reduced gold nanoparticles (SGNPs). i) Sgal is a chemical of sugar and esculetin molecules bridged by a glycosidic bond, which can be cleaved by βgal. Once it is cleaved, activated esculetin molecules bind to the closest auric ion and form a tri-esculetin ANM, in approximately 2 nm size. ii) Intact Sgal is similar to the conventional gold nanoparticle reducing agent, citrate in charge and chemical structure, but having four ring structures. Due to this aromatic molecular structure, the Sgal reaction rate is much higher than citrate. As a result, SGNPs are formed instantaneously at room temperature by simply mixing Sgal and auric ion solution.

In an aspect, described herein is an Sgal-reduced gold nanoparticle (SGNP) and synthesis technique that provides ultrafast particle formation and higher stability of SGNPs with an innate sensing capability for the βgalactosidase (βgal) enzyme (FIG. 1*ii*, 2). Described herein is a method to produce fresh SGNP in a minute with a sensing capability of one of the most popular reporter enzymes, βgal, simply by mixing Sgal and $HAuCl_4$ solutions at room temperature. While the method is applied to the synthesis of SGNPs, other reduced metal nanoparticles may be prepared by the methods described herein.

In an aspect, a method of making a reduced metal nanoparticle comprises mixing a reactive reducing agent with a metal salt in a solution at a temperature of 4° C. to 100° C., and forming the reduced metal nanoparticles in the solution. The nanoparticles form instantaneously, thus there is no need to wait for hours or days for the nanoparticles to form.

In an aspect, unlike conventional citric acid nanoparticle synthesis methods, the methods described herein do not include the use of acid-cleaned glassware, heating, and long incubation times.

Exemplary solutions are aqueous solutions. In an aspect, the reaction may be performed in an organic solvent such as ethanol, methanol, DMF, acetone, DMSO, and any other polar solvents, which have been reported as a solvent for $NaBH_4$. In an aspect, the reaction is performed at about room temperature, such as about 20° C. to about 25° C. At lower temperatures, the reaction is slower, however, higher concentrations of reagents can accelerate the reaction. Thus, the reaction speed can be adjusted by adjusting the temperature and the concentration of the reagents.

In an aspect, the metal nanoparticles such as SGNPs have diameters of 5 nm to 150 nm, specifically 5 nm to 50 nm for monodisperse particles. Size control can be achieved by mixing different concentrations of reagents at different temperatures. At temperatures of 4° C. to 100° C., particle size control can be achieved using concentration ratio manipulation.

Preferably, the nanoparticles are monodisperse nanoparticles, that is, the particles have a substantially uniform particle size such as 5-50 nm. In general, smaller particles have better monodispersity than large particles.

The reactive reducing agents used in the methods described herein are reactive with metal salts such as gold salts at room temperature. In an aspect, the reactive reducing agents are biologically active reducing agents such as esculetin salts.

Exemplary biologically active reactive reducing agents include 3,4-cyclohexeneoesculetin-B-D-galactopyranoside (3,4-cyclohexenoesculetin-β-D-galactoside, Sigma-Aldrich 57313, Sgal), 3,4-cyclohexenoesculetin-β-D-glucoside as disclosed in U.S. Pat. No. 6,287,798, or a water soluble salt thereof. A specific reducing agent is Sgal sodium salt.

Exemplary metal salts include gold, silver, gadolinium, erbium, thulium, ytterbium, copper, cobalt, palladium and nickel salts such as $AgNO_3$, $CuCl_2$, $NiCl_2$, $CoCl_2$, $Pd(Ac)_2$, gadolinium chloride ($GdCl_3$), ytterbium chloride ($YbCl_3$), thulium chloride ($TmCl_3$), Erbium chloride ($ErCl_3$), chloroauric acid ($HAuCl_4$), bromoauric acid ($HAuBr_4$), potassium tetrachloroaurate ($KAuCl_4$) $AuCl_3$, $AuF_3$, $AuBr_3$, and sodium tetrachloroaurate ($NaAuCl_4$).

In an aspect, the method comprises modifying and/or functionalizing the reduced metal nanoparticles. Exemplary modifiers include thiols, biotin, streptavidin, polyethylene glycol, amine groups, carboxyl groups, alkyl groups, peptides, DNA, RNA, antibodies, and combinations thereof. The modifications can themselves provide functionality to the gold nanoparticles, or functionalities can be linked through the modifier. Exemplary functionalities include dyes, biomolecules such as lectin, lactose and biotin, proteins, peptides, nucleic acids, antibodies and fragments thereof, therapeutic agents, and combinations thereof. Nucleic acids include aptamers, siRNA, antisense DNAs and RNAs, and the like.

In an aspect, a kit comprises a reactive reducing agent that is sensitive to β-galactosidase, a metal salt, and optionally a modifying agent/functionalizing agent for reduced metal nanoparticles. For example, a kit may contain Sgal and gold ion solutions in different concentrations, as well as a surface modification reagent, which can be mixed to conveniently generate the nanoparticles in need for the user's purposes, which can be either conventional or βgal sensitive.

In a specific aspect, described herein are SGNPs and methods of making SGNPs. In an aspect, the novel synthesis method described herein works from micro- to macro-volume at room temperature by simply mixing two reagents, $HAuCL_4$ sodium solution and 2,4 cyclohexeneoesculetin-B-D-galactopyranoside (S-Gal) sodium salt. The process does not require acid-cleaned glassware or sophisticated processes such as heating and timely mixing.

The method of making SGNPs described herein is useful not only for high-volume production, but also, for point-of-care and animal studies because it is a user-friendly one-step process which provides instantaneous reaction, stability in physiological conditions, innate sensitivity for the βgal enzyme, and higher robustness than conventional nanoparticles.

Specifically, Sgal has a higher reaction rate than the conventional reducing agent, sodium citrate, which provides the higher stability and fast and robust synthesis of nanoparticles, which makes the synthesis method simple and user-friendly. The one-step mixing of Sgal and $HAuCl_4$, for example, provides monodisperse SGNPs instantaneously at room temperature.

Without being held to theory, it is believed that the higher reaction rate between gold ion and Sgal also contributes to the stability of produced SGNPs. As a result, although the colloidal state of SGNP is rebalanced by the change of structure from monomer to dimer, the SGNPs are stable even in PBS. The stability of SGNPs in PBS is promising for applications under physiological conditions, which are critical for the biological investigations. In an aspect, the SGNPs are stable in PBS for at least four months at 4° C. As defined herein, stability is measured by UV-VIS spectroscopy, wherein the peak intensity may change, but the peak wavelength and bandwidth remain substantially constant.

In an aspect, a method of measuring βgalactosidase enzyme activity comprises contacting the SGNPs described herein with a sample suspected of containing βgalactosidase, and detecting a structural change in the SGNPs caused by the βgalactosidase. Exemplary structural changes include in vitro assays for colorimetric change such as by UV-VIS spectroscopy. Exemplary structural changes detectable in vivo include X-ray CT for gold nanoparticles and MRI for rare earth metals such as gadolinium.

Figure 1:
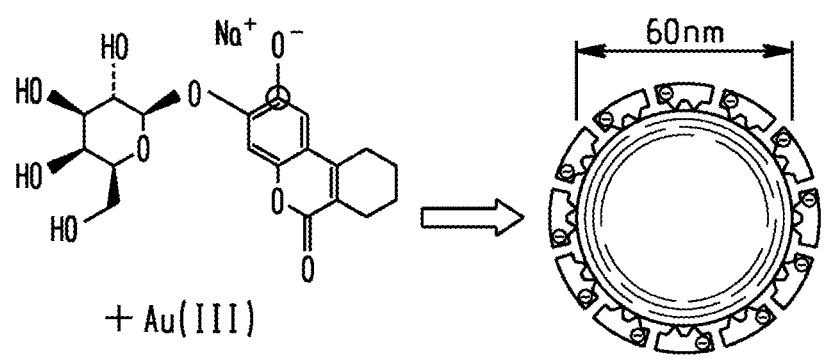
Figure 2:
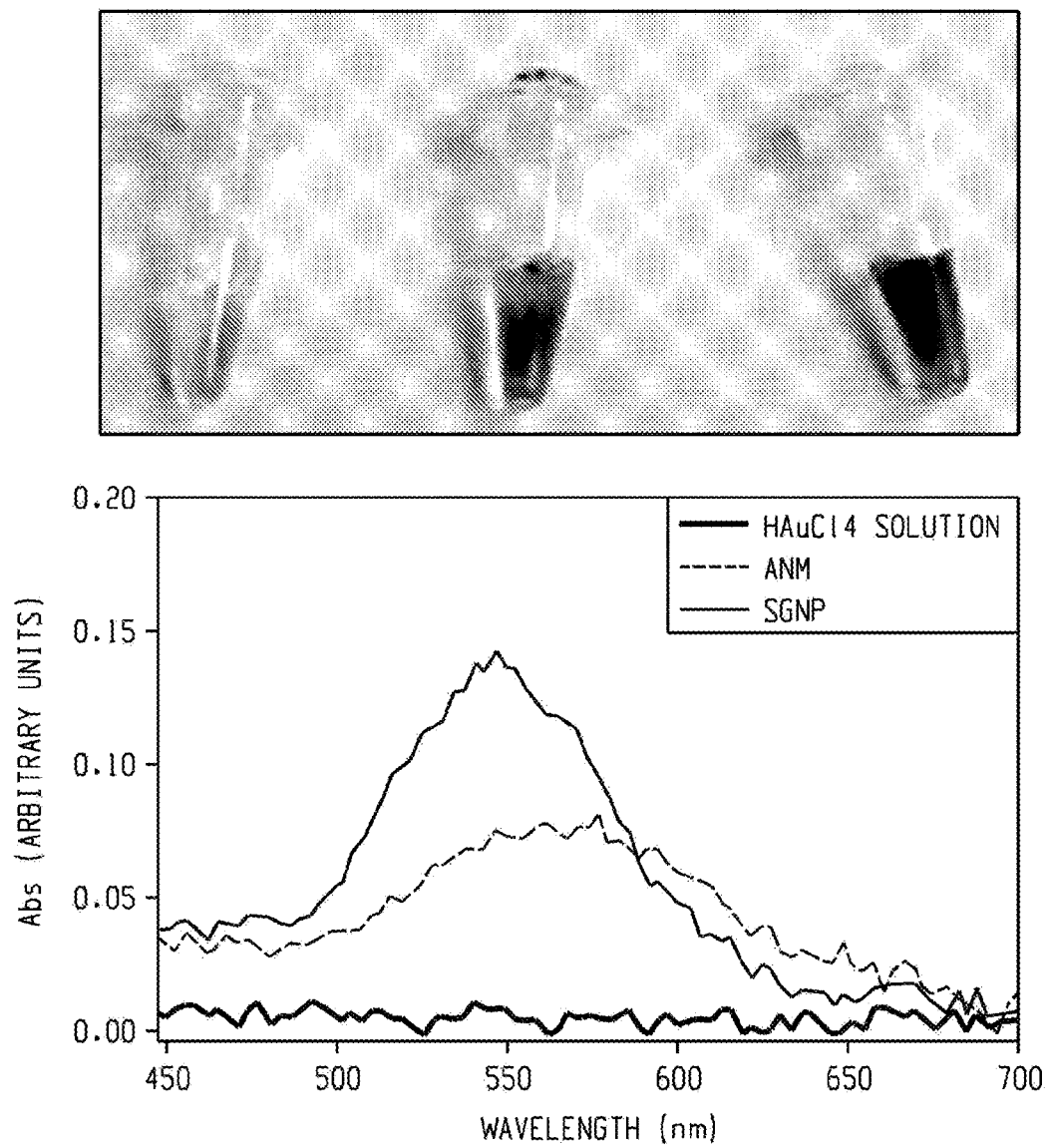
FIG. 2, top shows, from left, auric solution, ANM by cleaved Sgal, and SGNP by intact Sgal. The bottom shows UV-Vis spectra of three materials. Both top and bottom data show that ANM solution is dominantly uncontrolled aggregation, while the SGNP solution is a monodispersed and stable nanoparticle colloid.
Figure 3I:
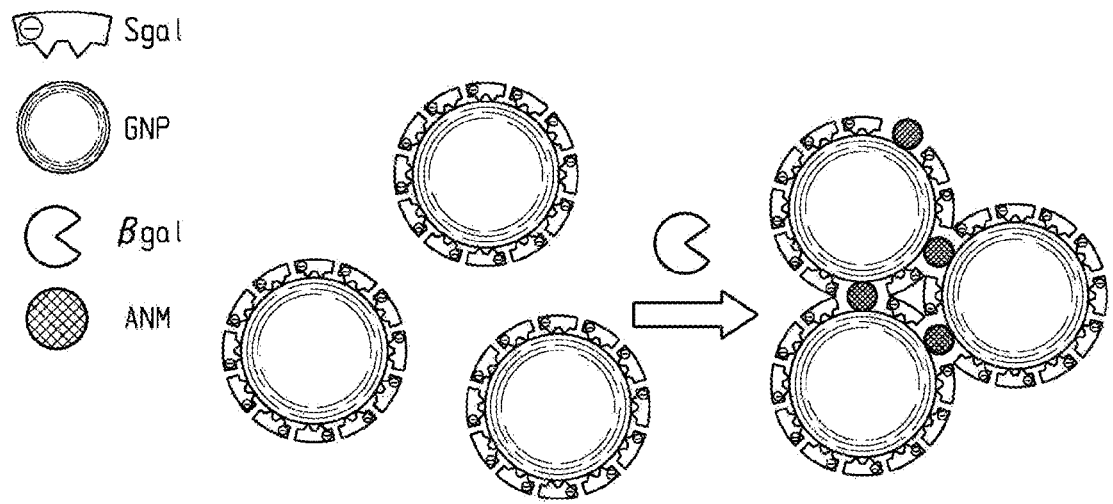
FIG. 3 shows βgal enzyme sensitivity and possible applications of SGNP. i) SGNP is reduced by intact Sgal, which is sensitive to the βgal enzyme. When βgal is present, the enzyme will cleave the glycosidic bond of Sgal, activating the ANM formation. Residual auric ion will participate, and the nanoparticles will form controlled weak-interacting multimers. In other words, the plasmonic resonance properties remain similar because the interparticle distance is not so close (>2 nm). ii) Possible applications of SGNP utilizing βgal sensitivity. The SGNP synthesis can be done in microvolumes without either high temperature or special equipment. By simply mixing Sgal and $HAuCl_4$ solutions, βgal-sensitive SGNP will be ready in a minute. Freshly made SGNP can be used for point of care or animal X-ray imaging depending on the βgal expression models.
Figure 3:
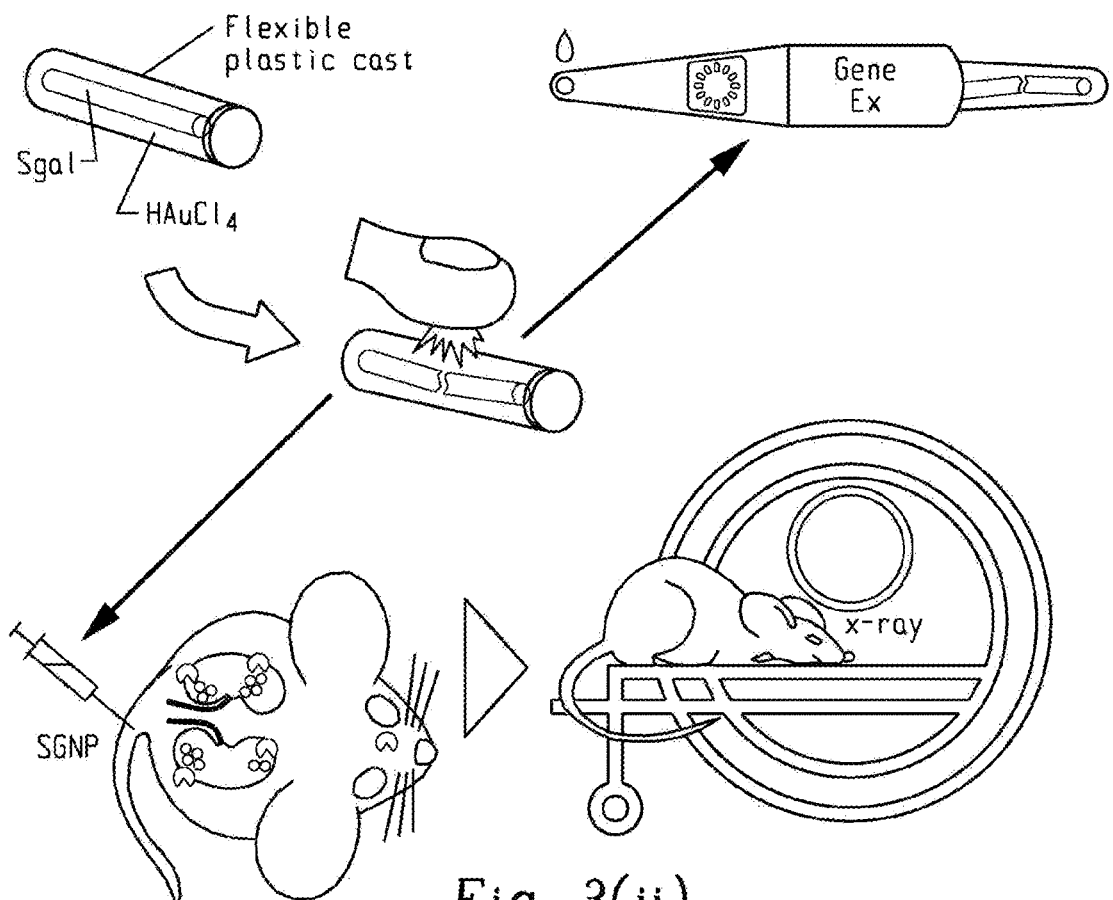
Figure 4:
FIG. 4 top and bottom show SNP with and without βgal in PBS and $H_2O$, respectively. Structure change is clear in the colorimetric measurements. In PBS, SGNPs form controlled strong-interacting multimers to rebalance the colloidal stability in the existence of strong ion screening in PBS. Since there is no linker structure, their interparticle distances are close, and the color shift is big. On the other hand, SGNPs with βgal form multimers linked by nanoparticles, making the interparticle distance longer. Thus, the interaction between nanoparticles is weak, and the resulting color shift is relatively small. In water, SGNPs without βgal remain a monomer colloid as prepared. However, SGNPs with βgal still form a controlled weak-interacting multimer, so there is a color shift. This demonstrates the colorimetric sensitivity for βgal enzymes and stability of SGNP.

An advantage is that the SGNPs have an innate sensitivity for the βgal enzyme because intact Sgal is exclusively sensitive to gal, while cleaved Sgal is sensitive to auric ions ($Au^{3+}$) to form auric nanomaterials (ANM) as shown in FIG. 1 i). Hence, βgal will cleave Sgal and form an $Au^{3+}$-sensitive Sgal, followed by a structural change of SGNP, resulting in a colorimetric shift (FIGS. 3, 4). Indeed, a clear color difference was observed with and without the existence of βgal in the solution. Since βgal is one of the most popular reporter enzymes for other biomolecule expressions, the innate sensitivity of the SGNPs for βgal is useful in various applications as a molecular sensor.

In addition, due to the high stability of SGNP, because the charge and structure of Sgal are similar to the prior art citrate, the SGNPs are available for all the conventional surface modification kits and methods.

Finally, since the SGNPs can measure the enzyme activity in PBS without toxicity, SGNPs can be injected into the mouse without further modification by tail vein injection and monitoring the βgal activity in the live mouse for the X-ray imaging as SGNP is visible in X-ray for imaging (FIG. 3 ii). Since X-ray images provide superior resolution compared to other in-vivo imaging modalities, impact of the invented SGNPs have the potential of providing new approaches of monitoring numerous important biomolecule expression in live animals in real time.

Overall, point-of-care application, stability in PBS, enzyme sensitivity, various modifications, and the potential use as an X-ray imaging agent are substantial advantages of SGNPs over any of the conventional gold nanoparticles.

The SGNPs are particularly useful for, but not limited to, monitoring a βgal enzyme activity in the micro-volume samples on a chip or similar point-of-care applications. Monitoring of βgal enzyme activity becomes more powerful when combined with various models using βgal as a gene expression reporter because it provides information about gene expression regulation depending on the conditions, for example, disease progress, such as cancer, aging, and neurodegeneration. Another promising application is in live animal imaging by X-ray. When the surface Sgal on the SGNPs is cleaved by βgal present in the mouse organs due to the gene expression, the SGNPs are prone to form a controlled network structure, which is distinctively localized in organs for a time sufficient to permit imaging, for example, using X-ray imaging Last but not least, in addition to these optimal uses for point-of-care and animal imaging, all conventional applications such as reagents for diagnostics, drug and gene delivery, imaging agents, in-vivo disease targeting, energy harvest, solar cells, battery, semiconductor, and catalysis are also equivalently possible because there is no notable difference between SGNP and the conventional gold nanoparticles in matters of surface modification and plasmonic functionality.

The invention is further illustrated by the following non-limiting examples.

EXAMPLES

Example 1: Synthesis of SGNPs

To prepare biologically active gold nanoparticles, 3,4-Cyclohexeneoesculetin-B-D-galactopyranoside (Sgal) was used as a reducing agent. Sgal is a non-toxic, cell membrane-permeable, and highly reactive substrate because of its aromatic chemical structure in both galactose and esculetin molecule bridged to each other by a glycosidic bond. A glycosidic bond can be cleaved exclusively by βgal, making Sgal a sensitive βgal sensor with the existence of ferric ions because it can form ferric nanomaterial aggregations when it is cleaved by βgal. Considering the popular uses of βgal as a reporter of other biomolecules, such as gene expression or a senescence marker, its highly reactive sensor, Sgal, became the reducing agent of gold nanoparticles (SGNP) as shown in FIG. 1 i). As shown schematically in FIG. 1 i), once the glycosidic bond bridging the sugar and esculetin is cleaved, activated esculetin molecules bind to the closest auric ion and form a tri-esculetin auric nanomaterial (ANM) of approximately 2 nm in size.

As shown in FIG. 1 ii), intact Sgal is similar to the conventional gold nanoparticle reducing agent, citrate in charge and chemical structure but having four ring structures. Due to this aromatic molecular structure, the Sgal reaction rate is much higher than citrate. As a result, SGNP is formed instantaneously by simply mixing Sgal and auric ion solution.

Example 2: Use of SGNPs to Detect βgal

SGNPs have an innate sensing capability making them useful for point-of-care and animal experiments. The Sgal of the SGNP is sensitive to βgal activity reporting of other biomolecules. In other words, when the SGNPs meet βgal in the physiological solution solution of approximately pH 7.4, the particles form a controlled aggregation, providing visual confirmation of βgal detection without any other equipment after certain incubation time (FIG. 3 i) and FIG. 4). As a proof of principle In FIG. 4, the quantity-controlled βgal enzyme activity was detected using both Sgal and SGNP. In short, SGNPs form multimers when the βgal enzyme hydrolyzes and activates chelation of the Sgal on the particle surface. As a result, the particles become more stable and its signal is colorimetrically shifted.

Advantages of the methods described herein and SGNPS include:
  A user-friendly, one-step synthesis that reduces process time to, for example, about a minute at room temperature without any advanced equipment.
  The SGNPs have innate sensitivity and specificity for beta-galactosidase enzyme activity, one of the most widely used reporter enzymes for molecular expression, such as mRNA and protein expression.

SGNPs provide higher colloidal stability than conventional nanoparticles; thus, the modification of the nanoparticle surface is robust and diverse.

SGNPs provide direct application under physiological conditions, such as in intracellular and animal models.

SGNPs include all functionalities of conventional citrate-reduced nanoparticles.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of making reduced metal nanoparticles, comprising:
   mixing a reactive reducing agent with a metal salt in a solution at a temperature of 4-100° C., wherein the reducing agent comprises 3,4-cyclohexenoesculetin-β-D-galactopyranoside or 3,4-cyclohexenoesculetin-β-D-glucoside, or a water-soluble salt thereof; and
   forming reduced metal nanoparticles in the solution.

2. The method of claim 1, wherein the method does not include the use of acid-cleaned glassware and heating.

3. The method of claim 1, wherein the reducing agent comprises 3,4-cyclohexenoesculetin-β-D-galactopyranoside (Sgal) sodium salt.

4. The method of claim 3, wherein the metal salt comprises $HAuCl_4$ and the nanoparticles are Sgal-reduced gold nanoparticles.

5. The method of claim 4, wherein the Sgal-reduced gold nanoparticles have diameters of 5 nm to 150 nm.

6. The method of claim 1, wherein the metal salt is a gold salt, a silver salt, a copper salt, a cobalt salt, a palladium salt, or a nickel salt.

7. The method of claim 1, wherein the metal salt is $AgNO_3$, $CuCl_2$, $NiCl_2$, $CoCl_2$, $Pd(Ac)_2$, $GdCl_3$, $YbCl_3$, $TmCl_3$, $ErCl_3$, chloroauric acid ($HAuCl_4$), bromoauric acid ($HAuBr_4$), potassium tetrachloroaurate ($KAuCl_4$) $AuCl_3$, $AuF_3$, $AuBr_3$, or sodium tetrachloroaurate ($NaAuCl_4$).

8. The method of claim 1, further comprising modifying and/or functionalizing the surface of the reduced metal nanoparticles.

9. The method of claim 8, comprising modifying the surface of the reduced metal nanoparticles with a thiol, biotin, streptavidin, polyethylene glycol, an amine group, a carboxyl group, an alkyl group, a peptide, DNA, RNA, or an antibody, or a combination thereof.

10. The method of claim 8, comprising functionalizing the surface of the reduced metal nanoparticles with a dye, a biomolecule, a protein, a peptide, a nucleic acid, an antibody, an antibody fragment, or a therapeutic agent, or a combination thereof.

* * * * *